United States Patent [19]
Sperbeck

[11] Patent Number: 5,471,036
[45] Date of Patent: Nov. 28, 1995

[54] GOGGLE DEFOGGING SYSTEM WITH TRANSPARENT INDIUM-TIN-OXIDE HEATING LAYER DISPOSED ON A LENS

[76] Inventor: Scott W. Sperbeck, 20007 - 45th Dr. SE., Bothell, Wash. 98012

[21] Appl. No.: 310,151

[22] Filed: Sep. 21, 1994

Related U.S. Application Data

[63] Continuation-in-part of Ser. No. 189,958, Jan. 31, 1994, Pat. No. 5,354,966, which is a continuation-in-part of Ser. No. 801,278, Dec. 2, 1991, abandoned.

[51] Int. Cl.$^6$ .................... A42B 1/08; H05B 3/00
[52] U.S. Cl. .................... 219/522; 219/543; 219/211; 2/435; 359/512
[58] Field of Search .................... 219/203, 522, 219/211, 543; 2/435, 6.3, 6.4, 6.7; 351/62; 359/512; 15/250.05; 128/201.15; 338/308, 309

[56] References Cited

U.S. PATENT DOCUMENTS

| | | | |
|---|---|---|---|
| 2,640,904 | 6/1953 | Gaiser | 219/522 |
| 3,024,341 | 3/1962 | Ogle, Jr. et al. | 219/522 |
| 3,027,561 | 4/1962 | Senne | 219/211 |
| 3,140,390 | 7/1964 | Smith et al. | 219/211 |
| 3,160,735 | 12/1964 | Aufricht | 219/211 |
| 3,173,419 | 3/1965 | Dubilier et al. | 219/211 |
| 3,330,942 | 7/1967 | Whitson | 219/541 |
| 3,495,259 | 2/1970 | Rocholl et al. | 219/522 |
| 3,718,535 | 2/1973 | Armstrong et al. | 428/339 |
| 3,878,361 | 4/1975 | Levin et al. | 219/522 |
| 3,982,092 | 9/1976 | Marriott | 219/203 |
| 4,209,234 | 6/1980 | McCooeye | 351/62 |
| 4,543,466 | 9/1985 | Ramus | 219/203 |
| 4,584,721 | 4/1986 | Yamamoto | 2/424 |
| 4,638,728 | 1/1987 | Elenewski | 219/211 |
| 4,682,007 | 7/1987 | Hollander | 219/211 |
| 4,868,929 | 9/1989 | Curcio | 2/435 |
| 4,878,850 | 11/1989 | Letemps et al. | 439/83 |
| 4,942,629 | 7/1990 | Stadlmann | 2/435 |
| 4,952,783 | 8/1990 | Aufderheide et al. | 219/528 |
| 4,957,358 | 9/1990 | Terada et al. | 359/512 |
| 5,119,467 | 6/1992 | Barsky et al. | 392/439 |
| 5,319,397 | 6/1994 | Ryden | 351/62 |
| 5,351,339 | 10/1994 | Reuber et al. | 219/211 |
| 5,354,966 | 10/1994 | Sperbeck | 219/203 |

FOREIGN PATENT DOCUMENTS

| | | | |
|---|---|---|---|
| 1285976 | 7/1991 | Canada | 2/435 |
| 58-160920 | 9/1983 | Japan | 351/62 |
| 3-27014 | 2/1991 | Japan | 351/62 |
| 4-276714 | 10/1992 | Japan | 351/62 |
| 636251 | 5/1983 | Switzerland | 2/435 |

*Primary Examiner*—John A. Jeffery
*Attorney, Agent, or Firm*—Christensen O'Connor Johnson & Kindness

[57] ABSTRACT

A goggle (11) that includes an electrical defogging system includes a frame (13) and a transparent lens (15). The transparent lens includes an outside layer (51 or 61) and inside layer (53 or 63) spaced from the outside layer by a peripheral gasket (55 or 65). The inside layer has an indium tin oxide (ITO) coating. The ITO coating includes an interior heating zone (33) that is electrically isolated from the edge of the inside layer. Silver bus bars (45, 47) are printed atop the ITO coating along the opposing edges of the interior heating zone adjacent the top and bottom of the goggle lens. The edge isolation regions and the bus bars are positioned and oriented such that the region (48) where the bus bars cross the nose area (41) of the goggle lens is isolated from the interior heating zone (33). Further, the bus bar that passes along the bottom of the goggle lens extends upwardly along one side of the lens. The side section of this bar is electrically isolated (39) from the interior heating zone. As a result, the bus bar only contacts the interior heating zone along the top of the goggle lens and along the bottom of the eye regions (37) of the goggle lens located on either side of the nose area (41).

18 Claims, 4 Drawing Sheets

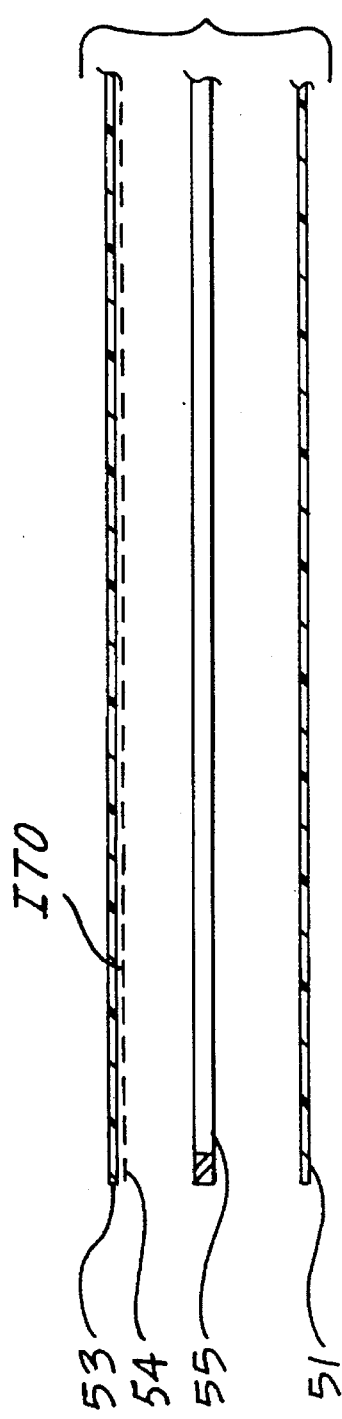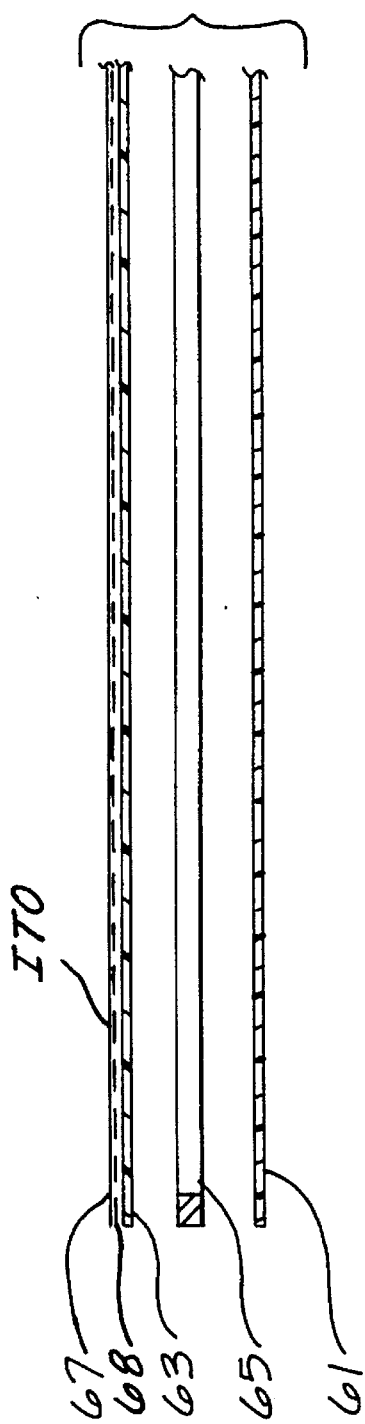

GOGGLE DEFOGGING SYSTEM WITH TRANSPARENT INDIUM-TIN-OXIDE HEATING LAYER DISPOSED ON A LENS

CROSS-REFERENCE TO OTHER APPLICATIONS

This application is a continuation-in-part of U.S. patent application Ser. No. 08/189,958, filed Jan. 31, 1994, now U.S. Pat. No. 5,354,966, and entitled WINDOW DEFOGGING SYSTEM WITH OPTICALLY CLEAR OVERLAY HAVING MULTI-LAYER SILVER BUS BARS AND ELECTRICALLY ISOLATING PERIPHERAL GROOVES, which is a continuation-in-part of U.S. patent application Ser. No. 07/801,278, filed Dec. 2, 1991, now abandoned and entitled HEATED WINDOW SYSTEM. The subject matter of application Ser. Nos. 07/801,278 and 08/189,958 is incorporated herein by reference.

TECHNICAL AREA

This invention is related to defogging systems and, more particularly, to heating systems for defogging goggles.

BACKGROUND OF THE INVENTION

It is well known that windows and windshields, such as those incorporated in motorcycle helmets, can be defogged by applying heat. In general, two approaches have been utilized to heat windows and helmet shields. One approach is to mount a pair of spaced-apart bus bars connected together by a plurality of thin wires on a transparent substrate. An alternative approach is to replace the thin wires with a layer of indium tin oxide (ITO). Depending upon the application, the transparent substrate is adhesively attached to, or mechanically mounted on, the window or helmet shield to be defrosted. Examples of such systems applied to helmet shields are described in U.S. Pat. Nos. 3,024,341; 4,584,721 and 4,682,007. For various reasons, the use of ITO to defog helmet shields has not been entirely satisfactory.

Ski and other goggles, like windows and helmet shields, frequently have fogging problems. Originally, ski goggle lenses, as many other goggles, were formed of a single layer of transparent plastic material mounted in a frame. In order to reduce fogging, air passageways were created in the frames of ski goggles. Unfortunately, snow, particularly wet snow, quickly reduces the effectiveness of such air holes. Another way of reducing the fogging of ski goggles that has been used in the past is to make the lens of multiple transparent layers separated by a dead air space. While the foregoing and other approaches have reduced ski goggle fogging, they have not entirely eliminated this problem. Depending upon their use, other goggles also can have fogging problems.

The present invention is directed to providing ski and other goggles that incorporate a heating system for defogging the lens of the goggles.

SUMMARY OF THE INVENTION

In accordance with this invention, goggles that include an electrical defogging system are provided. The goggles include a frame and a transparent lens housed in the frame. The lens includes an outside layer and an inside layer spaced from the outside lens by a peripheral gasket. The inside layer has an indium tin oxide (ITO) coating. The ITO coating includes an interior heating zone that is electrically isolated from the edge of the inner layer. The interior heating zone of the ITO coating can be electrically isolated by scoring a groove around the periphery of the ITO coating. Alternatively, acid etching can be used to remove a peripheral part of the ITO coating. Multiple layers of silver are primed atop the ITO coating, along opposing edges of the interior heating zone adjacent to the top and bottom of the goggle lens to create bus bars. The edge isolation regions and the bus bars are positioned and oriented such that the region where the bus bars cross the nose area of the goggle layer is isolated from the interior heating zone. Further, the bus bar that passes along the bottom of the goggle layer extends upwardly along one side of the layer. The side section of this bus bar is electrically isolated from the interior heating zone. As a result, the bus bars only contact the interior heating zone along the top of the goggle layer and along the sections of the goggle layer located on either side of the nose area.

In accordance with further aspects of this invention, the ITO coating is located on and forms part of the inside layer. The coating is located on the surface of the inside layer that faces the outside layer.

In accordance with alternative aspects of this invention, the ITO coating is located on a separate sheet of heat-stabilized polyester having a hard-coat on the surface opposite the ITO coating. The ITO coating is covered with an adhesive that is used to adhesively attach the sheet of heat-stabilized polyester to the outer surface of the inside layer of the goggle lens.

In accordance with other alternative aspects of this invention, the ITO coating is located on a separate sheet of heat-stabilized polyester having a hard coat on the surface opposite the ITO coating. The ITO-coated surface has adhesive located along its edges for adhesively attaching the separate sheet to the inside surface of a single-layer lens to create a double-layer lens wherein space exists between the ITO-coated surface of the layer formed by the separate sheet and the inside surface of the original single-layer lens.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is an exploded partial view illustrating the edge of one version of the lens of a goggle formed in accordance with the invention;

FIG. 4 is an exploded, partial view illustrating the edge of an alternate version of the lens of a goggle formed in accordance with the invention;

DETAILED DESCRIPTION OF THE PREFERRED EMBODIMENT

As will be better understood from the following description, while the invention was developed for use in defogging the lens of a ski goggle, the invention can also be used to defog the lens of other types of goggles.

Figure 1:
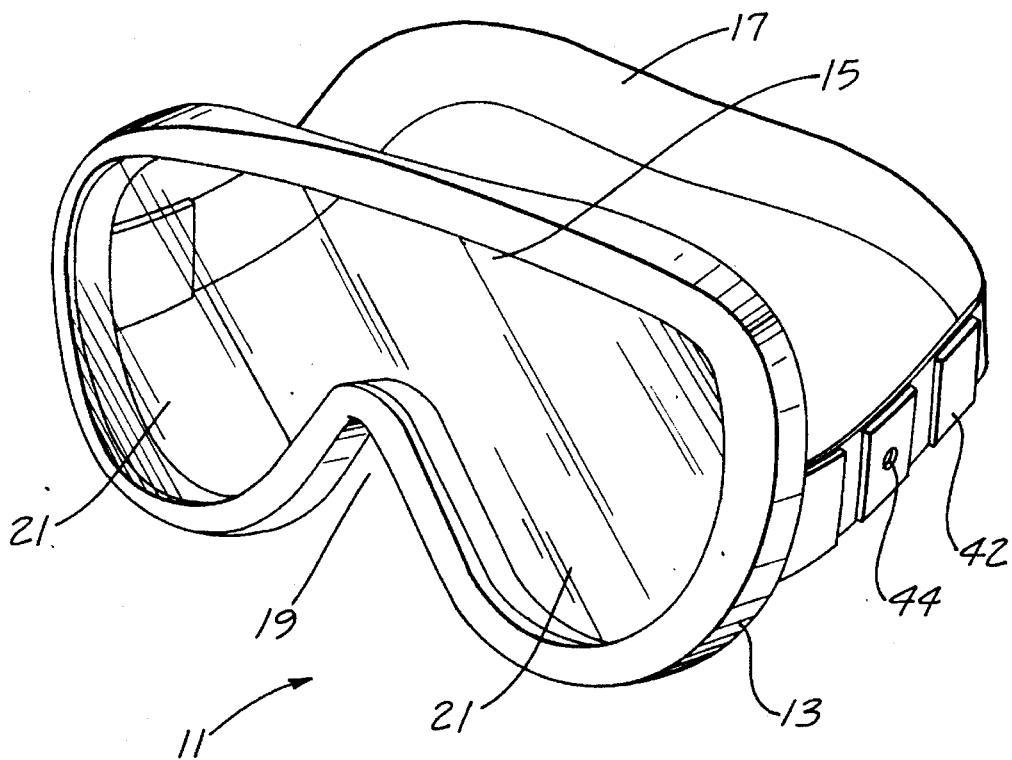
FIG. 1 is an isometric view of a ski goggle incorporating a lens formed in accordance with the invention.

FIG. 1 illustrates a typical ski goggle 11 incorporating a lens formed in accordance with this invention. The ski goggle 11 shown in FIG. 1 includes a frame 13, a lens 15, and a head strap 17. The frame 13 includes a nose area 19 located between a pair of teardrop-shaped eye regions 21 through which a skier looks. The lens includes a corresponding nose area. The head strap 17 is connected to either side of the frame 13. Usually the head strap 17 includes a mechanism (not shown) for shortening and lengthening the strap so that the ski goggle can be used with people of varying head sizes.

As is well known to those familiar with ski goggles, the ski goggle lens 15 typically comprises a pair of spaced-apart transparent layers separated by a peripheral gasket, usually formed of a foam-like material. Like sunglasses, one or both of the layers may be timed to filter out undesired light rays, such as ultraviolet (UV) rays. The lens 15 is usually removable from the frame 13 so that the lens can be replaced in the event the layers that make up the lens become cracked or broken and/or to allow lenses with different types of light passing capabilities to be used.

Some ski goggle lenses include a plurality of peripheral holes located along the top of the lens to allow air to enter the region between lens layers so that moisture can evaporate. Other lenses are completely sealed. In most instances, the frame 13 includes a plurality of peripheral edge apertures (not shown) that allow air to enter the region between a user's face and the lens to allow moisture to evaporate from this region.

One of the problems with prior art ski goggles is that the use of lens and frame air holes has not entirely eliminated fogging problems. Under some skiing circumstances, usually when the moisture content of falling snow is relatively high, ski goggles can be easily fogged. The present invention is directed to providing a ski goggle that is substantially fog free. As will be better understood from the following description, this result is accomplished by heating the interior layer of the lens 15. Heating is accomplished by adding an indium tin oxide (ITO) coating to the layer and applying electric power to bus bars deposited on the ITO coating. The ITO coating can be directly applied to the interior layer of the lens 15 during the manufacture of the goggles 11 or the ITO coating can be added to an existing goggle by coating a heat-stabilized polyester layer with ITO and adhesively attaching the heat-stabilized polyester layer to the interior layer of the lens 15. In either case, the ITO coating is processed in a way that electrically isolates an interior region of the ITO coating from the edge of the ITO coating. Further, the bus bars are deposited in a way that reduces the likelihood that hot spots will occur in the ITO coating when power is applied to the ITO coating.

Figure 2A:
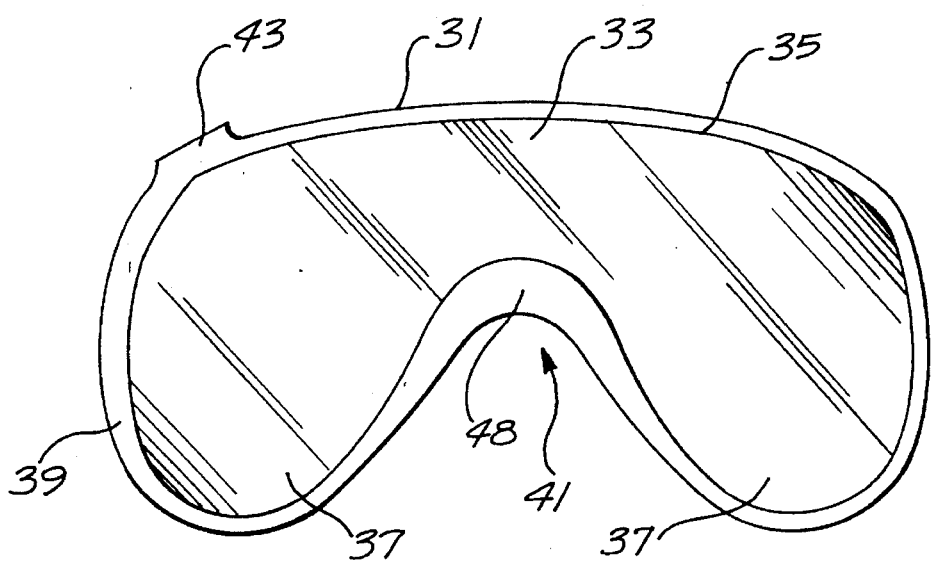
FIGS. 2A–2C are a series of views showing how an ITO layer suitable for use in the lens of a goggle formed in accordance with the invention is created.
Figure 2B:
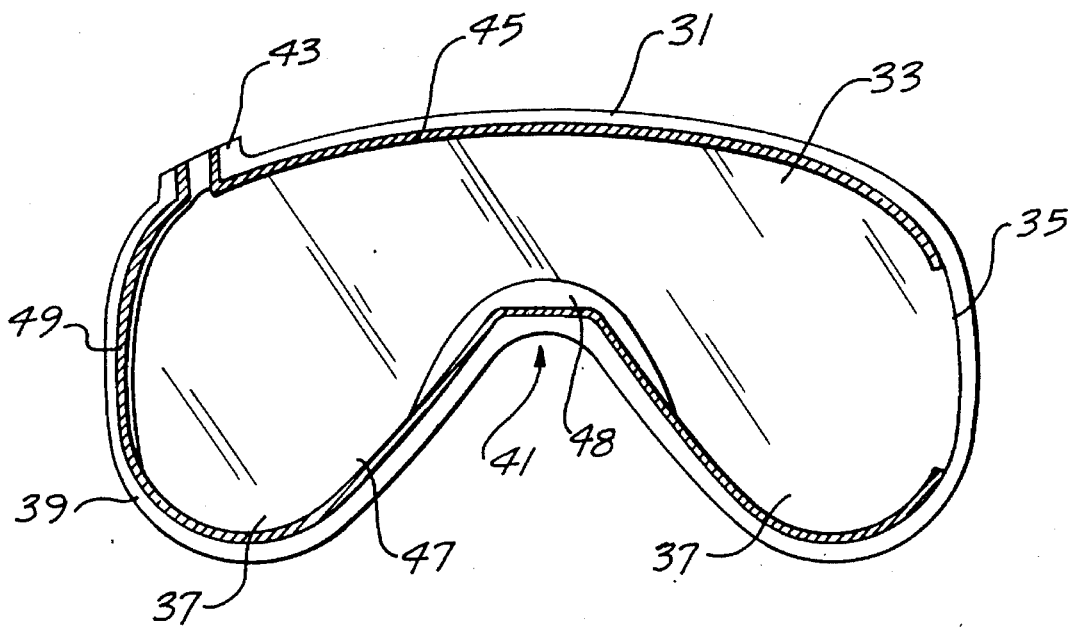
Figure 2C:
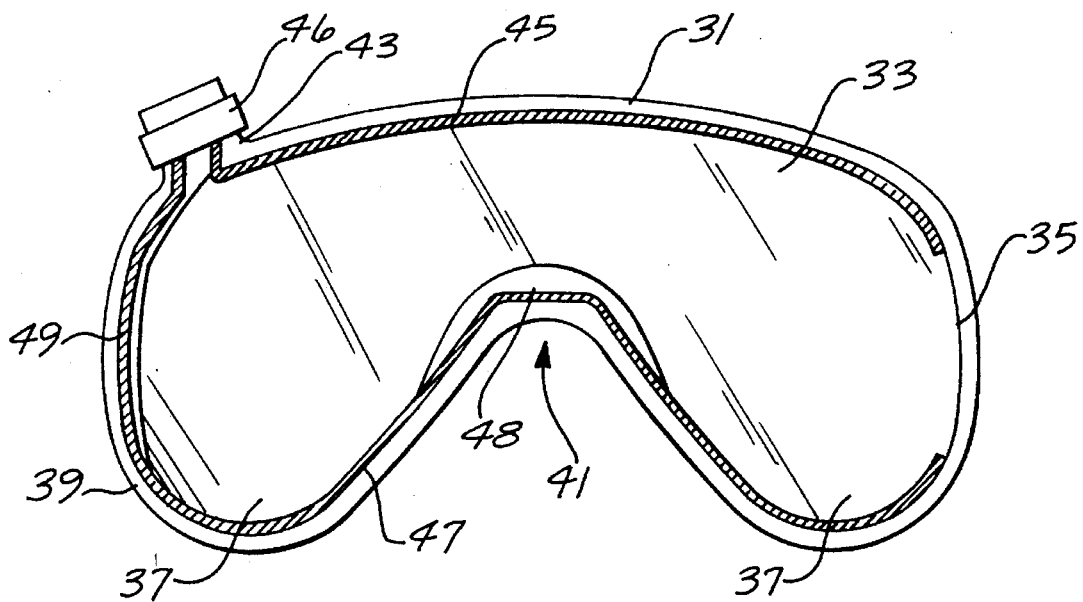

FIGS. 2A–2C illustrate how an interior heating zone is created in an ITO coating located either on the interior layer of a goggle lens or on a separate optically clear sheet of heat-stabilized polyester suitable for adhesive attachment to the interior layer of a goggle lens. Direct application to the interior layer is desirable when the invention is being incorporated into a goggle during manufacture. A separate sheet of adhesively attachable heat-stabilized polyester supporting an ITO coating is useful for after-market applications of the invention.

FIG. 2A illustrates a substrate 31 having an eyeglass shape, which can be the interior layer of a goggle lens coated with ITO or a separate optically clear sheet of heat-stabilized polyester that has ITO on one surface and, preferably, a hard-coat on the other surface. Initially, an interior heating zone 33 is created in the ITO coating that is electrically isolated from the edge of the substrate 31. The interior heating zone 33 of the ITO coating can be electrically isolated from the edge of the substrate 31 by scoring a groove 35 around the periphery of the ITO coating. Alternatively, acid etching can be used to remove the part of the ITO coating located around the periphery of the substrate 31. Along the top of the substrate 31 and at the bottom of the eye regions 37, the groove or removed portion is relatively near the edge of the substrate. Likewise, along one side of the substrate the groove or removed portion is relatively near the edge of the substrate. A larger width of ITO is removed or the score line is located more inwardly along the other side 39 of the substrate 31. Likewise, in the top of the nose region 41, the score line or removed portion extends more inwardly from the edge than along the top of the substrate and the bottom of the eye regions 37. Preferably, the substrate 35 includes a tab region 43 near the top that is either isolated from the interior heating zone 33 by a groove or from which the ITO coating is entirely removed. The tab is located on the same side of the substrate 31 as the more inwardly located score line.

After a groove has been created around the edge of the ITO coating and/or the edge portion of the ITO coating has been removed, as shown in FIG. 2B, a pair of bus bars are laid atop the ITO coating. One bus bar, the upper bus bar 45, is laid near the top of the substrate 31 along the upper edge of the interior heating zone 33. The upper bus bar 45 terminates in the tab region 43. Located along the lower edge of the substrate 31 is a lower bus bar 47. The lower bus bar lies atop interior heating zone 33 in the eye regions 37. In the nose region 41 the lower bus bar 47 is isolated from the interior heating zone of the ITO coating by crossing the removed area or isolated area 48 of the ITO coating that is located at the top of the nose region 41. The lower bus bar 47 includes a coupling bus bar 49 that terminates in the tab region 43. The coupling bus bar 49 is electrically isolated from the interior heating zone 33 by passing over the wider removed or isolated end 39 of the ITO coating 33. As a result of the way the bus bars are isolated from the interior heating zone 33, electrical connection between the interior heating zone 33 and the upper and lower bus bars 45 and 47 only occurs along the top of the interior heating zone and along the bottom of the teardrop regions 37 of the interior heating zone. This configuration avoids the creation of short electrical paths, such as between the top of the nose region 41 and the upper bus bar, which might cause hot spots to occur in the ITO coating when electrical power is applied to the bus bars.

Preferably, the tab 43 supports an electrical connector 46 (FIG. 2C) that is conductively connected to the upper and lower bus bars 45 and 47. The electrical connector is connected to a suitable power supply 42 and time-out switch 44 that are diagrammatically shown as mounted on the goggle strap 17 in FIG. 1. Obviously, these items could be mounted in the frame, if desired. The time-out switch allows power to be applied to the bus bars for a predetermined time after the switch is manually closed.

The nature of the substrate 31 is determined by whether the invention is to be incorporated into a goggle during manufacture or produced as an aftermarket part for application to existing goggles. FIG. 3 illustrates how the invention is incorporated into ski goggles during manufacture. Specifically, as shown in FIG. 3, a typical ski goggle lens includes a transparent outside layer 51 and a transparent inside layer 53 connected to and spaced from the outside layer by a peripheral gasket 55. Preferably the peripheral gasket is formed of a foam, plastic, or rubber material. In an original equipment embodiment of the invention, the substrate 31 shown in FIGS. 2A–2C forms the inside layer 53. The ITO coating 54 is located on the interior surface of the inside layer and, preferably, the exterior surface has a clear hard-coat layer. Further, preferably, the inside layer is a heat-stabilized polyester layer.

FIG. 4 illustrates an "aftermarket" version of the invention. Like FIG. 3, FIG. 4 illustrates a system formed by an outside transparent layer 61, an inside transparent layer 63 and a peripheral gasket 65. In this case, the substrate 31, shown in FIGS. 2A–2C and described above, is formed by a separate sheet of heat-stabilized polyester 67 having a hard coat on one surface. Located on the other surface is the ITO coating 68. The ITO coating 68 faces the inside layer 63 and is adhesively attached thereto by a suitable adhesive.

The invention can also be used with a single-layer original lens. More specifically, embodiments of the invention designed for use with a single-layer original lens include a second lens formed in the manner illustrated in FIG. 4 and described above. However, rather than the entire surface of the ITO coating being covered with an adhesive, only the periphery of the ITO coating is covered with an adhesive. As a result, when attached to the inside of the original single lens, a small space, in the few-thousandths-of-an-inch range, exists between the original single lens and the add-on ITO-coated substrate.

The bus bars 45 and 47 are formed of silver. However, rather than comprising a single layer of silver, as clearly shown in FIGS. 5 and 6, each bus bar comprises multiple layers of silver 71a, 71b and 71c, or 81a and 81b. Multiple layers are used because one mil is the maximum thickness of silver that can be applied using conventional screen printing processes. A one rail silver bar has inadequate current carrying capabilities for use in many commercially acceptable versions of the invention. Two or three layers of silver create a bus bar having a two or three mil thickness, which is normally adequate.

Figure 6:
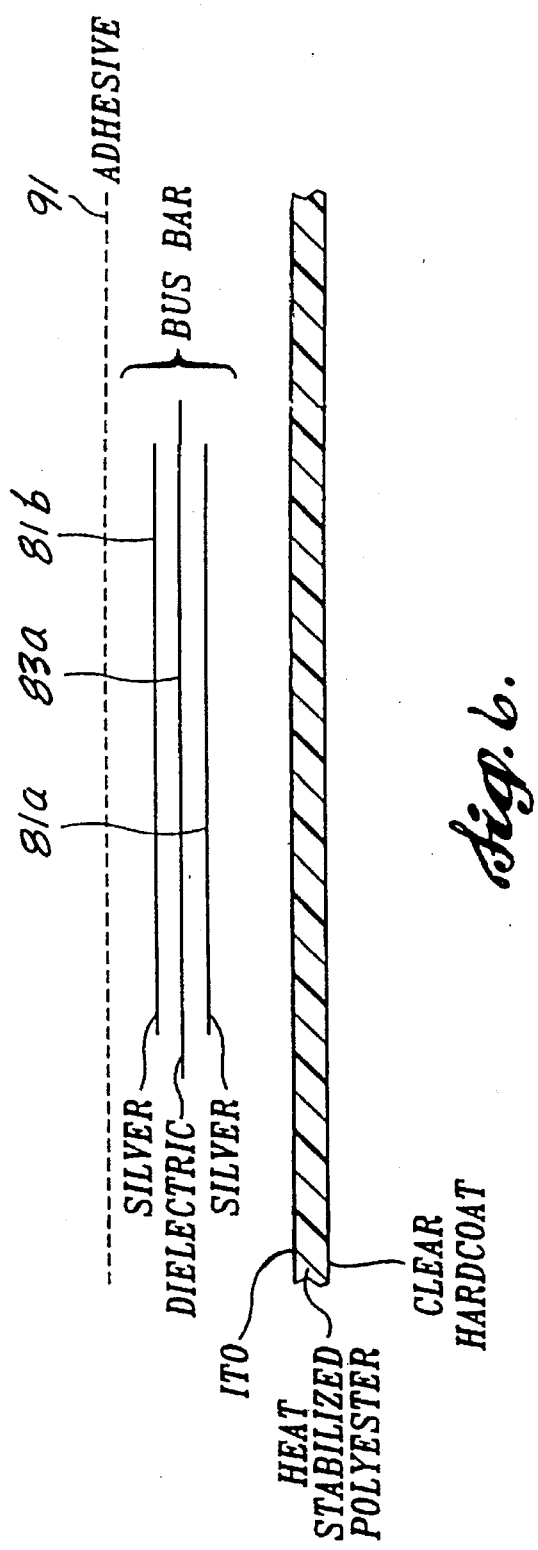
FIG. 6 is an exploded, cross-sectional view of the details of an alternate way of creating an ITO layer suitable for use in a goggle lens formed in accordance with this invention.

Because bus bars of the embodiments of the invention illustrated and described above extend along the entire length of the top and bottom edges of the interior heating zone 33, the voltage at the far end of the bus bars may be slightly less than the voltage at the point where electric power is applied to bus bars. The voltage difference is, of course, due to the voltage drop along the length of the bus bar. The drop in voltage can result in a slightly decreased current flow through the ITO coating located between the remote ends of the bus bars when compared to the current flow though the ITO coating at the end where power is applied. The differential in current flow through the ITO coating can decrease the heat generated at the remote ends of the bus bars and, thus, provide reduced defogging at the remote ends of the bus bars. This can be overcome by increasing the power applied to the bus bars. An alternative way is to add dielectric layers between a portion of the layers of the bus bars to create a bus bar arrangement where substantially the same voltage is applied to both ends of the bus bars. More specifically, the just-described voltage drop and resulting heat differential can be reduced, if not entirely eliminated, by adding a dielectric layer in the manner illustrated in FIG. 6. More specifically, after the first (or second) silver layer 81a has been printed to fore the bus bars, a layer of dielectric 83a is laid atop a part of the silver layers of each bus bars. The dielectric layer is slightly wider than the width of the bus bar. The dielectric layer 83 starts at a position near the terminal regions of the bus bars and extends along the bus bars, terminating a substantial distance from the remote ends of the bus bars. Therefor, as shown in FIG. 6, one or more additional layers of silver 81b are printed both atop the previously printed layers of silver and atop the dielectric layer. Thus, the additional layers of silver extend from the regions where power is applied to the bus bars to the remote ends of the bus bars. As a result, some of the applied power flows directly to the remote ends of the bus bars. In essence, power is applied to both ends of the portions of the bus bars that underlie the dielectric layer 83.

Figure 5:
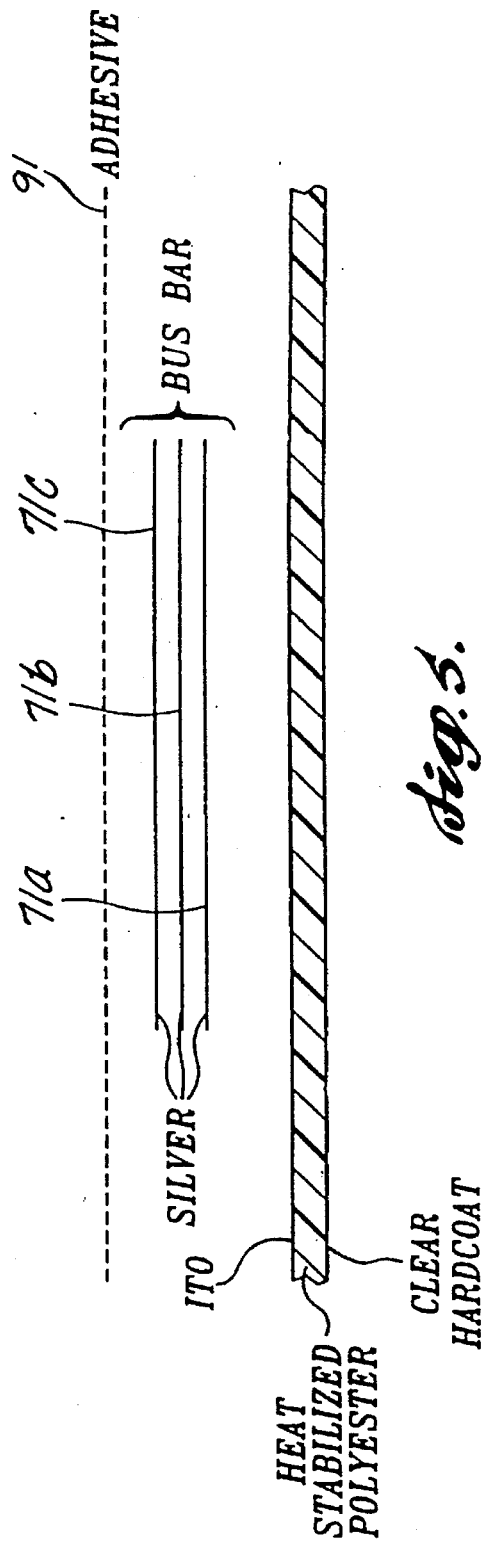
FIG. 5 is an exploded cross-sectional view of the details of how an ITO layer of a goggle lens formed in accordance with the invention is created.

As shown in phantom in FIGS. 5 and 6, after the bus bars are created, a layer of adhesive 91 may be applied atop the ITO coating. Such an arrangement forms the aftermarket ski goggle embodiment of the invention illustrated in FIG. 4. In situations where the invention is incorporated into a ski goggle during the manufacture, an adhesive layer is unnecessary because the ITO coating is directly applied to the inner layer of the ski goggle lens, as described above.

As can be readily understood from the foregoing description, when power is applied to the bus bars, heat is generated as current flows through the ITO coating. The heat generated defogs the lens of the ski goggles.

While preferred embodiments of the invention have been illustrated and described, it will be appreciated that various changes can be made therein without departing from the spirit and scope of the invention. Specifically, as noted above, the invention can be used with goggles other than ski goggles that are used in environments where the goggles become fogged. Consequently, within the scope of the appended claims, it is to be understood that the invention can be practiced otherwise than as specifically described herein.

The embodiments of the invention in which an exclusive property or privilege is claimed are defined as follows:

1. A goggle defogging system for a goggle including a frame and a lens housed in the frame, said lens including an inner layer and an outer layer held in a spaced-apart relationship, said frame and said lens including a nose region, said goggle defogging system comprising:

(a) an indium tin oxide (ITO) coating located on said inner layer of said lens, said ITO coating including an interior heating zone electrically isolated from the edge of said inner layer of said lens, said interior heating zone including the eye regions of said inner layer of said lens;

(b) a pair of bus bars located along opposing edges of said interior heating zones such that one bus bar lies near the upper edge of said inner layer of said lens and said other bus bar lies near the lower edge of said eye regions, said other bus bar being isolated from said interior heating zone in said nose region of said inner layer of said lens; and (c) an electrical power supply coupled to said bus bars.

2. The goggle defogging system claimed in claim 1, wherein said bus bars are formed of multiple layers of silver deposited atop said ITO coating.

3. The goggle defogging system claimed in claim 2, including a dielectric layer located between said multiple layers of silver of each of said bus bars along a length of the length of said bus bars.

4. The goggle defogging system claimed in claim 1, wherein said ITO bus bar that lies near the lower edge of said eye regions extends up one side of said inner layer of said lens crossing a region that is isolated from said interior heating zone.

5. The goggle defogging system claimed in claim 4, wherein said bus bars are formed of multiple layers of silver deposited atop said ITO coating.

6. The goggle defogging system claimed in claim 5, including a dielectric layer located between said multiple layers of silver of each of said bus bars along a length of the length of said bus bars.

7. The goggle defogging system claimed in claim 1, wherein said ITO coating is located on the surface of said inner layer facing said outer layer of said lens.

8. The goggle defogging system claimed in claim 7, wherein said bus bars are formed of multiple layers of silver deposited atop said ITO coating.

9. The goggle defogging system claimed in claim 8, including a dielectric layer located between said multiple layers of silver of each of said bus bars along a length of the length of said bus bars.

10. The goggle defogging system claimed in claim 7, wherein said ITO bus bar that lies near the lower edge of said eye regions extends up one side of said inner layer of said lens crossing a region that is isolated from said interior heating zone.

11. The goggle defogging system claimed in claim 10, wherein said bus bars are formed of multiple layers of silver deposited atop said ITO coating.

12. The goggle defogging system claimed in claim 11, including a dielectric layer located between said multiple layers of silver of each of said bus bars along a length of the length of said bus bars.

13. The goggle defogging system claimed in claim 1, including a transparent heat-stabilized polyester substrate and wherein said ITO coating is located on one surface of said heat-stabilized polyester substrate and wherein said surface is adhesively attached to the outer surface of the inner layer of said lens.

14. The goggle defogging system claimed in claim 13, wherein said bus bars are formed of multiple layers of silver deposited atop said ITO coating.

15. The goggle defogging system claimed in claim 14, including a dielectric layer located between said multiple layers of silver of each of said bus bars along a length of the length of said bus bars.

16. The goggle defogging system claimed in claim 13, wherein said ITO bus bar that lies near the lower edge of said eye regions extends up one side of said inner layer of said lens crossing a region that is isolated from said interior heating zone.

17. The goggle defogging system claimed in claim 16, wherein said bus bars are formed of multiple layers of silver deposited atop said ITO coating.

18. The goggle defogging system claimed in claim 17, including a dielectric layer located between said multiple layers of silver of each of said bus bars along a length of the length of said bus bars.

* * * * *

UNITED STATES PATENT AND TRADEMARK OFFICE
CERTIFICATE OF CORRECTION

PATENT NO.   : 5,471,036
DATED        : November 28, 1995
INVENTOR(S)  : S.W. Sperbeck It is certified that error appears in the above-indentified patent and that said Letters Patent is hereby corrected as shown below:

| COLUMN | LINE | |
|---|---|---|
| 2 | 5 | "primed" should read --printed-- |
| 3 | 18 | "timed" should read --tinted-- |
| 5 | 35 | "rail" should read --mil-- |
| 5 | 64 | "fore" should read --form-- |
| 6 | 3 | "Therefor," should read --Thereafter,-- |

Signed and Sealed this

Fourteenth Day of May, 1996

Attest:

BRUCE LEHMAN

Attesting Officer

Commissioner of Patents and Trademarks